(12) United States Patent
Luo

(10) Patent No.: US 12,313,197 B1
(45) Date of Patent: May 27, 2025

(54) HOSE CONNECTOR WITH AN ADJUSTMENT STRUCTURE

(71) Applicant: DCSTAR INC, New York, NY (US)

(72) Inventor: David Luo, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

(21) Appl. No.: 18/416,135

(22) Filed: Jan. 18, 2024

(51) Int. Cl.
*F16L 33/02* (2006.01)
*A61M 16/08* (2006.01)
*F16L 25/00* (2006.01)
*F16L 37/02* (2006.01)

(52) U.S. Cl.
CPC ......... *F16L 33/02* (2013.01); *A61M 16/0816* (2013.01); *F16L 25/0036* (2013.01); *F16L 25/0045* (2013.01); *A61M 16/0875* (2013.01); *F16L 37/02* (2013.01)

(58) Field of Classification Search
CPC ... F16L 25/0036; F16L 25/0045; F16L 37/02; F16L 21/007; F16L 47/20; F16L 37/04; A61M 16/0816; A61M 16/0875
See application file for complete search history.

(56) References Cited

U.S. PATENT DOCUMENTS

| | | | | |
|---|---|---|---|---|
| 2,315,792 | A * | 4/1943 | Hoss ..................... | F16L 37/02 |
| 3,243,206 | A * | 3/1966 | Samer | |
| 3,900,220 | A * | 8/1975 | Buchser | |
| 4,013,309 | A * | 3/1977 | Quick ..................... | F16L 47/20 |
| 4,110,144 | A * | 8/1978 | Buehler ................. | F16L 37/02 |
| 4,415,389 | A * | 11/1983 | Medford ............. | F16L 25/0036 |
| 4,625,998 | A * | 12/1986 | Draudt ................. | F16L 25/0036 |
| 5,287,851 | A * | 2/1994 | Beran ................. | A61M 16/0816 |
| 6,318,761 | B1 * | 11/2001 | Robertson ............. | F16L 21/007 |
| 6,692,035 | B2 * | 2/2004 | Baruh | |
| 9,784,387 | B2 * | 10/2017 | Kaye .................. | A61M 16/0875 |
| 9,808,593 | B1 * | 11/2017 | Ramanathan ..... | A61M 16/0816 |
| D805,630 | S * | 12/2017 | Formica | |
| D948,027 | S * | 4/2022 | Babbage | |
| 2010/0116272 | A1 * | 5/2010 | Row .................. | A61M 16/0875 |
| 2013/0264821 | A1 * | 10/2013 | Duck ...................... | F16L 37/02 |
| 2023/0313925 | A1 * | 10/2023 | Wong .................. | F16L 25/0045 |

FOREIGN PATENT DOCUMENTS

WO    WO-2017094807 A1 *  6/2017

OTHER PUBLICATIONS

WO-2017094807-A1—Machine Translation—English (Year: 2017).*

* cited by examiner

*Primary Examiner* — William S. Choi
(74) *Attorney, Agent, or Firm* — HSML P.C.

(57) ABSTRACT

A hose connector with an adjustment structure to securely connect patient interface components to a machine in Continuous Positive Airway Pressure therapy. The hose connector includes a first connector end to connect an external tubular connector, a second connector end to connect a hose, and a sidewall that encircles and forms the first connector end and the second connector end. The sidewall has an interior and an exterior, with a gripping portion on the exterior. The first connector end, which is configured to connect to the external tubular connector, includes a portion of the sidewall, a chamber that is configured to accommodate the hose connector, an opening, an abutment surface, and a retaining structure. At least one adjustment structure is provided on the opening. Furthermore, the first connector end of the hose connector with the adjustment structure is made of a resilient first material.

19 Claims, 16 Drawing Sheets

HOSE CONNECTOR WITH AN ADJUSTMENT STRUCTURE

TECHNICAL FIELD

The present disclosure pertains to treatments or improvements for respiratory-related conditions, providing a hose connector with an adjustment structure. This connector ensures a sealed connection between the patient interface component and the machine during CPAP therapy, offering enhanced usability.

BACKGROUND

Obstructive Sleep Apnea Syndrome (OSAS) is a sleep disorder caused by obstructive lesions in the upper respiratory tract. It is defined as an adult experiencing at least 30 instances of breathing pauses lasting at least 10 seconds each, or an average of more than 5 breathing pauses per hour during 7 hours of nighttime sleep. OSAS manifests as loud snoring, brief gasps, and recurring breathing pauses lasting 10 seconds or more during sleep. Breathing pauses can lead to a sense of suffocation, occasional sudden awakenings, and a return to sleep after breathing is restored. This significantly impacts sleep quality, with patients often experiencing fatigue, daytime sleepiness, and, in chronic cases, anxiety and depression. Repetitive episodes of hypoxia during sleep can damage various organs, leading to complications in the cardiovascular, respiratory, nervous, endocrine, and urinary systems. OSAS severity is categorized into mild, moderate, and severe, with the primary goal of treatment being to increase the tension in the respiratory airway, facilitating normal gas exchange by bringing oxygen from the external environment into the body and expelling carbon dioxide generated by metabolism to the external environment. The five common treatment approaches for OSAS include adopting healthy lifestyle habits, medication, Continuous Positive Airway Pressure (CPAP), oral appliances, and surgical interventions. Among these, CPAP therapy is the preferred choice for many. Patients are required to wear corresponding devices connected to machines providing positively pressurized gas, ensuring an ample supply of pressurized gas to patients for proper breathing.

The design of hose connectors in the equipment poses several challenges. a. Sealing: The connector of the hose needs to be able to seal and connect to external components, ensuring that gas does not leak during the transmission process, thus maintaining the effectiveness of positive pressure ventilation therapy. b. Sturdiness: During the sleep process, patients move, causing the hose connector to also move. If the hose connector is not securely connected to the external component, it is prone to detachment under external force, potentially compromising the continuity of CPAP machine therapy for the patient. c. Ease of use: Some existing products in the market, to enhance the sealing of the hose connector, reduce its inner diameter, making it tighter when connecting to external components. However, this also makes it difficult for the hose connector to connect to external components. Or some hose connectors have connectors made of rigid materials such as polyethylene, polypropylene, polycarbonate, etc. While these materials are stable, they have characteristics that make them resistant to deformation, making it difficult for the hose connector to connect easily to external components. d. Durability: The outer diameter of external components in the market is usually 15 mm or 22 mm. Therefore, the connector of existing hose connectors usually has a slightly larger inner diameter than the outer diameter of the external components in the patient assembly. The purpose is to smoothly connect the external component to the hose connector. Some hose connectors are typically made of flexible materials. Due to the frequent installation, disassembly, and use of the equipment, flexible materials are prone to fatigue deformation or material aging, gradually losing elasticity and affecting the sealing. Patients are forced to replace the hose connector to maintain the airtightness of the treatment process.

Therefore, to obtain hose connectors that are more sealed, sturdier, user-friendly, and more durable, it is essential to focus on the design of hose connectors, considering their shape, size, and other comprehensive aspects.

SUMMARY

Based on this, it is necessary to provide a hose connector with an adjustment structure to address the above-mentioned shortcomings.

In one embodiment, a hose connector with an adjustment structure is provided. The hose connector has the following features:

The hose connector includes a sidewall that is configured to encircle and form a first connector end and a second connector end and that is provided with an interior and an exterior, with the exterior having a gripping portion.

The first connector end, configured to connect to an external tubular connector, includes a chamber to house the external tubular connector, an opening to allow the external tubular connector to enter the chamber, and an abutment surface to limit a displacement of the external tubular connector.

The second connector end, configured to connect to a hose, includes a space to accommodate the hose.

At least one adjustment structure is provided on the opening.

The first connector end is made of a resilient first material, and the first connector end has a non-uniform wall thickness from the abutment surface to the opening, with the wall thickness being greater at the abutment surface than at the opening.

In one embodiment, an inner diameter of the opening of the first connector end does not exceed 22 mm.

In one embodiment, an overall height range of the hose connector is at or between 15 to 45 mm.

In one embodiment, the wall thickness at the opening of the first connector end is not less than 2 mm.

In one embodiment, an inner diameter of the second connector end is less than or equal to an inner diameter of the first connector end.

In another embodiment, a hose connector with an adjustment structure is provided.

The hose connector includes a sidewall that is configured to encircle and form a first connector end and a second connector end and that is provided with an interior and an exterior, with the exterior having a gripping portion.

The first connector end, configured to connect to an external tubular connector, includes a chamber to house the external tubular connector, an opening to allow the external tubular connector to enter the chamber, and a retaining structure to enhance fixation ability.

The second connector end, configured to connect to a hose, includes a space to accommodate the hose.

At least one adjustment structure is provided on the opening.

The retaining structure has one or more of the following characteristics:

a. having an inner diameter less than or equal to an outer diameter of the external tubular connector;
b. protruding toward a central axis of the hose connector;
c. being in an inverted cone shape;
d. a material of the retaining structure being a second material.

In one embodiment, an inner diameter of the second connector end is less than or equal to an inner diameter of the first connector end.

In one embodiment, a height of the retaining structure in an inverted cone shape is equal to a depth of the chamber.

In one embodiment, a maximum inner diameter of the retaining structure in an inverted cone shape is less than or equal to the outer diameter of the external tubular connector.

In one embodiment, the depth of the chamber is at least 12 mm.

In one embodiment, a protruding height of the protruding retaining structure is less than the depth of the chamber.

In yet another embodiment, a hose connector with an adjustment structure is provided.

The hose connector includes a sidewall that is configured to encircle and form a first connector end and a second connector end and that is provided with an interior and an exterior, with the exterior having a gripping portion.

The first connector end, configured to connect to an external tubular connector, includes a chamber to house the external tubular connector, an opening to allow the hose connector to enter the chamber, and an abutment surface to limit a displacement of the hose connector.

The second connector end, configured to connect to a hose, includes a space to accommodate the hose.

At least one adjustment structure is provided on the opening.

An inner diameter of the second connector end is less than or equal to an inner diameter of the first connector end, and a depth of the chamber is at least 12 mm.

In one embodiment, the inner diameter of the first connector end is less than or equal to an outer diameter of the external tubular connector.

In one embodiment, the first connector end has a retaining structure and an inner diameter of the retaining structure is less than the inner diameter of the first connector end.

In one embodiment, the gripping portion is in the form of a recess or protrusion. In one embodiment, the adjustment structure takes the form of a notch and a depth of the notch does not exceed ½ of the depth of the chamber.

In an embodiment, another hose connector with an adjustment structure is provided, which includes a sidewall that is configured to encircle and form a first connector end and a second connector end and that is provided with an interior and an exterior, with the exterior having a gripping portion.

The first connector end, configured to connect to an external tubular connector, includes a chamber to house the external tubular connector, an opening to allow the hose connector to enter the chamber, and an abutment surface to limit a displacement of the hose connector;

The second connector end, configured to connect to a hose, includes a space to accommodate the hose.

The first connector end is made of a resilient first material.

At least one adjustment structure is provided on the opening, and the adjustment structure has one or more of the following characteristics:
a. having a depth not exceeding ½ of a depth of the chamber;
b. having a width less than ⅔ of an inner diameter of the opening.

In one embodiment, the adjustment structure takes the form of a notch or a third material different from the first material.

In one embodiment, an inner diameter of the first connector end is less than or equal to an outer diameter of the external tubular connector.

In one embodiment, a root of the adjustment structure has an arc shape.

The hose connector with an adjustment structure provided herein has at least the following beneficial effects:

1) The design of the adjustment structure addresses a common issue in many hose connectors, where the inner diameter of the connector is typically larger than the external diameter of the connected external component (including the external tubular connector). This design ensures a smooth connection between the external component and the hose connector. To enhance the durability of the hose connector, some hose connectors opt for rigid materials like polyethylene, polypropylene, polycarbonate, or other plastic materials. However, to improve user experience and product comfort, others choose elastic materials such as silicone, rubber, or other thermoplastic elastomers, which offer softness and strong deformation capabilities. Therefore, using rigid materials does not provide a better experience than using elastic ones, but elastic materials are prone to fatigue deformation or material aging due to repeated stress loading and unloading as the connector needs frequent installation and disassembly with external components, gradually losing their original shape and elasticity, leading to seal failure and slippage. This disclosure innovatively combines the principle of notch effect by incorporating an adjustment structure with a certain depth and width at the opening of the first connector end. This design facilitates deformation when connecting to the external tubular connector. The notch effect causes stress concentration at the discontinuous opening when the external tubular connector contacts the discontinuous opening with an adjustment structure. This stress concentration at the opening reaches the yield strength of the material, resulting in elastic deformation in the region near the root of the adjustment structure. This leads to a larger opening to accommodate the external component quickly and easily. Through reasonable material selection and design, the adjustment structure can return to its original size and shape after expansion, ensuring a sealed connection with the external component. This provides a comfortable user experience, effective sealing, and an extended lifespan for the hose connector during patient use of the hose connector. The connector of the hose connector is made from an elastic material that feels comfortable, and the inner diameter of the connector is configured to be less than or equal to the outer diameter of the external component. At least one adjustment structure is provided on the opening:

a. In comparison to hose connectors on the market that reduce the inner diameter of the connector, the connector described herein is provided with at least one adjustment structure, and the inner diameter is less than or equal to the outer diameter of the external component. While ensuring the ability to provide the same level of extension of the hose connector's lifespan, this design offers a flexible structure, enhancing the operability and adaptability of the connector. It allows connectors that are originally equal or slightly smaller in inner diameter to deform into a larger opening through the adjustment structure, facilitating smooth entry of the external component and preventing issues arising from the inner diameter of the connectors being too small to connect to other external components.

b. In contrast to hose connectors on the market that enlarge the inner diameter of the connector, the connector discussed herein has a larger proportion of an effective sealing portion within the connector. Many hose connectors on the market, due to the enlargement of the inner diameter of the connector, allow a smooth connection to external components but may result in a certain distance between the effective sealing portion and the end surface. This indirectly reduces the proportion of the effective sealing portion in the chamber accommodating the external connector. However, the connector with at least one adjustment structure ensures that the sealing portion occupies one hundred percent of the chamber containing the external connecting component, increasing the contact area with the external component and achieving a better sealing effect.

2) The installation and disassembly experimental validation of the connector of the hose connector with the structural design of the adjustment structure, combined with material selection, can prolong the service life of the connector. Due to the use of elasticity materials that can deform, the elastic material of the connector undergoes fatigue deformation due to prolonged and frequent installation and disassembly, leading to the loosening of the connector and the inability to achieve sealing. Therefore, in the design provided herein, the inner diameter of the connector is configured to be smaller than or equal to the outer diameter of the external component. The extended lifespan of the hose connector means that users can reduce the frequency of replacing the hose connector, making it more economical for them. Additionally, this reduction in replacement frequency leads to less waste disposal, making it more environmentally friendly.

DETAILED DESCRIPTION

To make the objectives, features, and advantages of the present disclosure more clear and understandable, a detailed description of the specific embodiments of the disclosure is provided below in conjunction with the accompanying drawings. In the following description, many specific details are laid out to ensure a full understanding of the disclosure. However, it is apparent that the disclosure can be implemented in different ways than those described herein, and those skilled in the art can make similar modifications without departing from the spirit of the disclosure. Therefore, the disclosure is not limited to the specific embodiments disclosed below.

Figure 13:
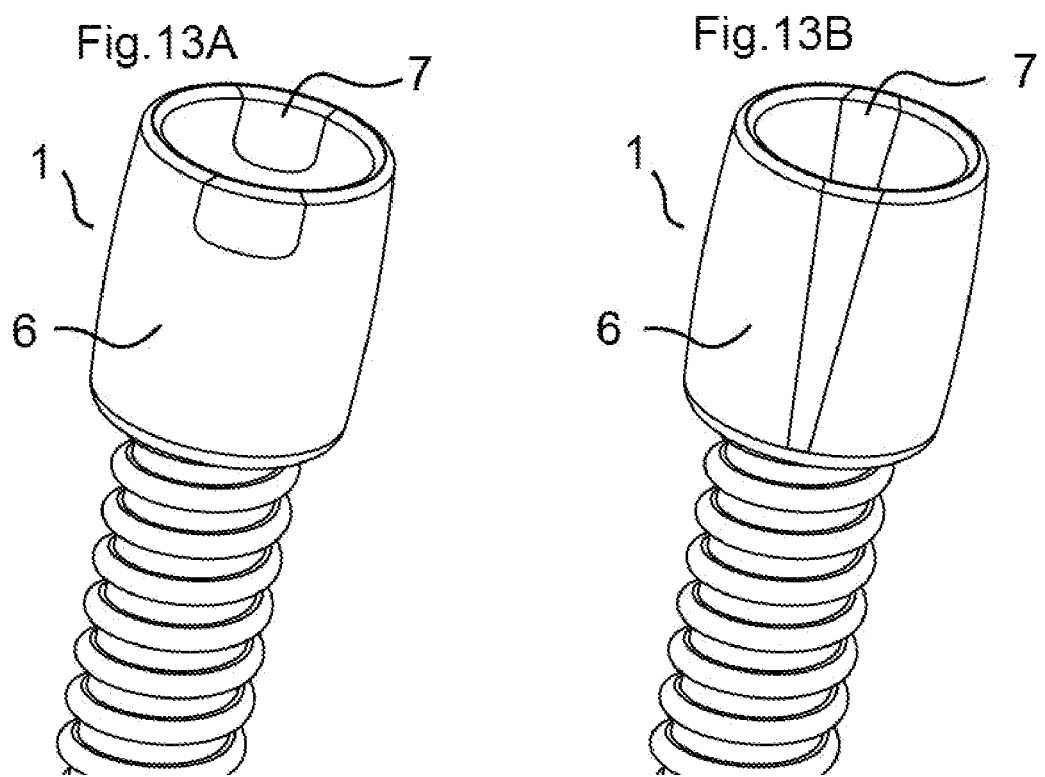
FIG. 13A and FIG. 13B are structural schematic diagrams illustrating different structures of a hose connector in accordance with an example embodiment.
Figure 14:
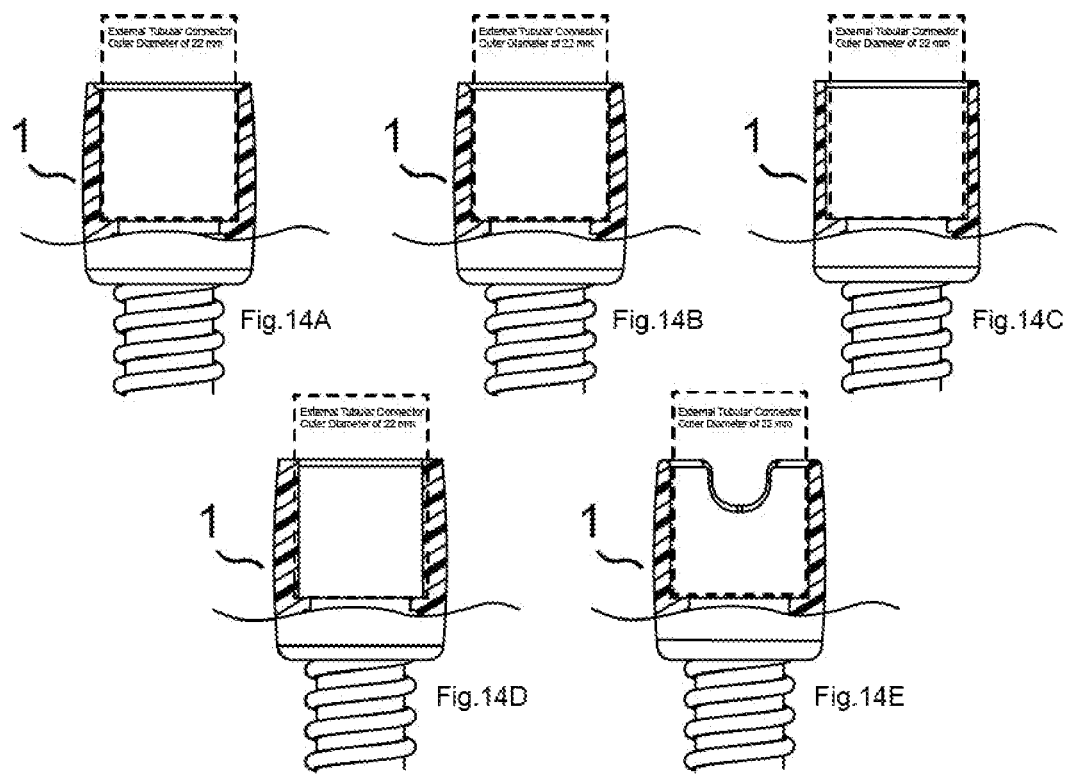
FIG. 14 is a schematic diagram showing step a for the installation and disassembly experiment described herein.
Figure 15:
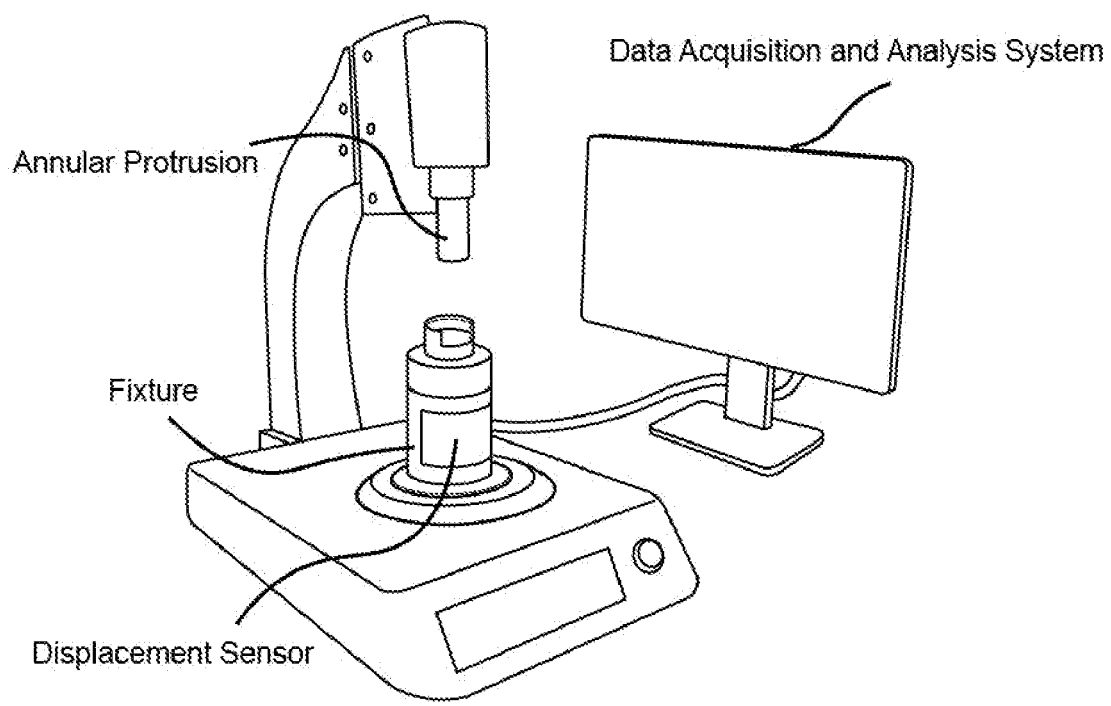
FIG. 15 is a schematic diagram of the experimental apparatus for the installation and disassembly experiment described herein.
Figures 16A, 16B:
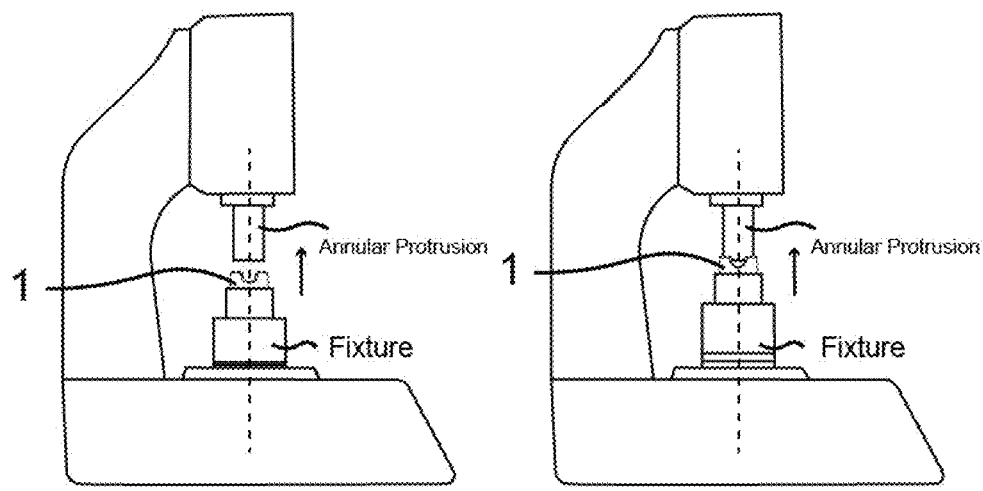
FIGS. 16A. 16B are another schematic diagrams of the experimental apparatus for the installation and disassembly experiment described herein.

The disclosure discussed herein, combining the notch design in structural design, analyzes and considers the internal and external forces on the hose connector and the material properties, to ensure the structural stability of the connector of the hose connector and its resistance to fatigue damage. The disclosure discussed herein conducts experiments on the durability of the connector by installation and disassembly, following the principles of comparison and the controlled variable method. The experimental procedure is roughly as follows:

a. Prepare the necessary equipment and experimental materials, which include five models of hose connectors depicted in FIG. 13 (These models include the following: Resmed-Climateline Air™ and Philips Respironics-DreamStation, which have chamfered end surfaces on the connector; a plastic connector made of rigid materials; Standard CPAP Hose, which has an inner diameter of the end surface on the connector that is less than or equal to 22 mm; and the hose connector described herein, with an adjustment structure on the end surface and an inner diameter less than or equal to 22 mm, all with chambers of identical depth to accommodate external components. The necessary equipment and experimental materials, as shown in FIG. 14, also include testing instruments (with an annular protrusion of the outer diameter that is 22 mm and a fixture with displacement sensors for installation), a computer, or a data acquisition and analysis system.

b. Simulate a scenario where a patient uses the hose connectors, maintaining a consistent environment of temperature (25±3° C.) and humidity (40%-50%). Five different models of hose connectors are individually configured as five experimental comparison groups (Group A for Resmed-ClimatelineAir™, Group B for Philips Respironics-DreamStation, Group C for the plastic connector, Group D for Standard CPAP Hose, Group E for the hose connector with an adjustment structure). The hose connectors in each of the five experimental comparison groups are measured for the thrust distance of the connector in the vertical direction under the same force (e.g., 50N) and the degree of deformation of the inner diameter after multiple installations and disassemblies. This ensures that the testing equipment meets the following requirements: identical testing equipment models and debugging parameters (i.e., force during installation, force during disassembly, 360 cycles); the initial position of the fixture is the same (i.e., the distance of the fixture from the annular protrusion is the same).

c. The initial inner diameter of the opening of the hose connectors in each of the five experimental comparison groups is measured, and the data is recorded.

d. As shown in FIG. 15, the hose connectors are fixed in the same position to the fixture of the testing instrument, ensuring that the axis of the hose connectors at the fixture coincides with the axis of the annular protrusion.

e. The testing instrument drives the hose connectors to repetitively install and disassemble according to the same set procedure, and the displacement sensor of the fixture measures the displacement data of the fixture in the experiment, recording the results.

f. Remove the hose connectors after completing the installation and disassembly experiments. Measure the inner diameter of the hose connectors in each of the five experimental comparison groups after the tests and record the data for comparison with the initial inner diameter.

g. Repeat the experiments with each sample in every group more than three times, and replicate the above experimental steps more than three times to avoid chance occurrences.

h. Data analysis: 1. The fixture displacement value is highest in Group E, moderate in Groups A, B, and C, and lowest in Group D. 2. After the experiments, the measured inner diameter is the smallest in Groups D and E, the second smallest in Group C, and the largest in Groups A and B. The conclusion is that the connector with an adjustment structure and an inner diameter equal to or smaller than the outer diameter of the external component in Group E is the most durable.

The comparison through data calculation shows that a connector with an adjustment structure 221 and an inner diameter less than or equal to the outer diameter of an external component can effectively prolong the lifespan of the hose connector by about 30%.

Figure 1:
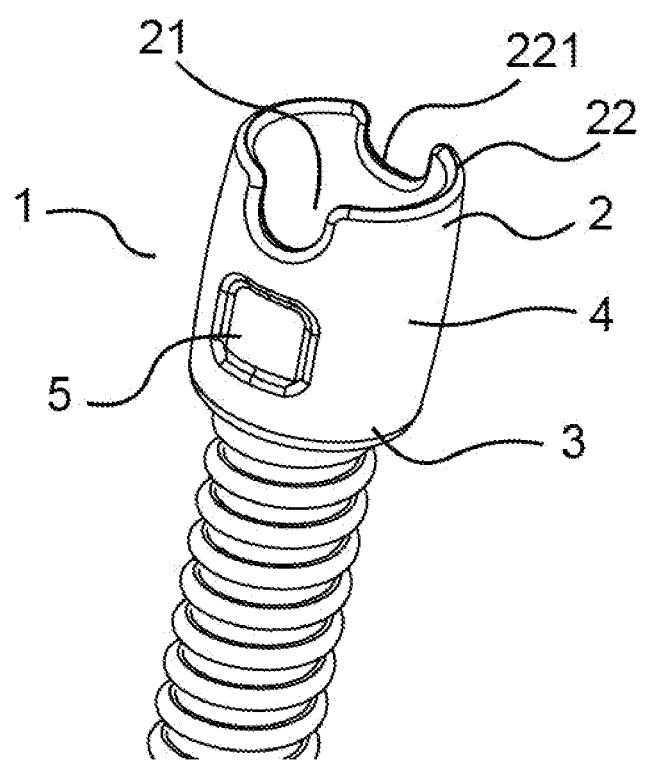
FIG. 1 is a structural schematic diagram of a hose connector with an adjustment structure in accordance with an example embodiment.
Figure 2:
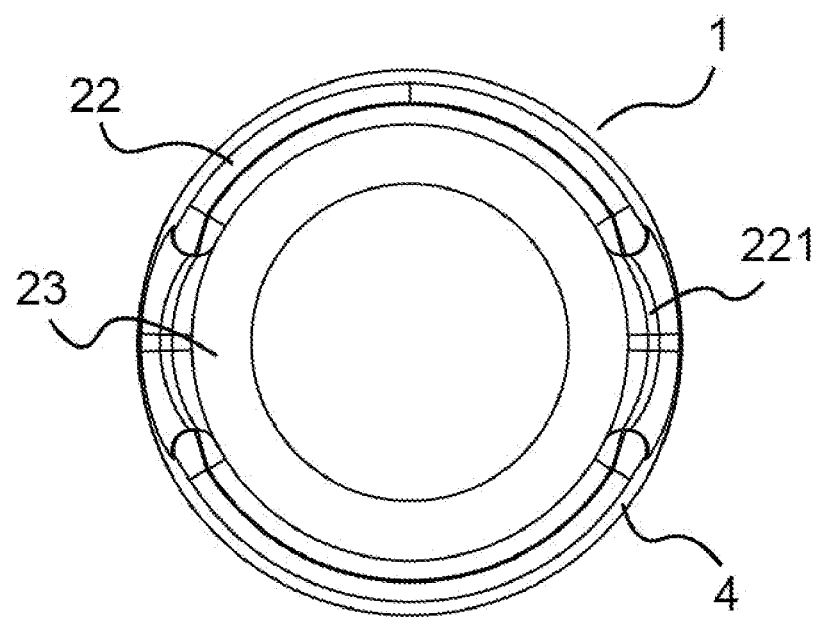
FIG. 2 is a top view of a hose connector with an adjustment structure in accordance with an example embodiment.
Figure 3:
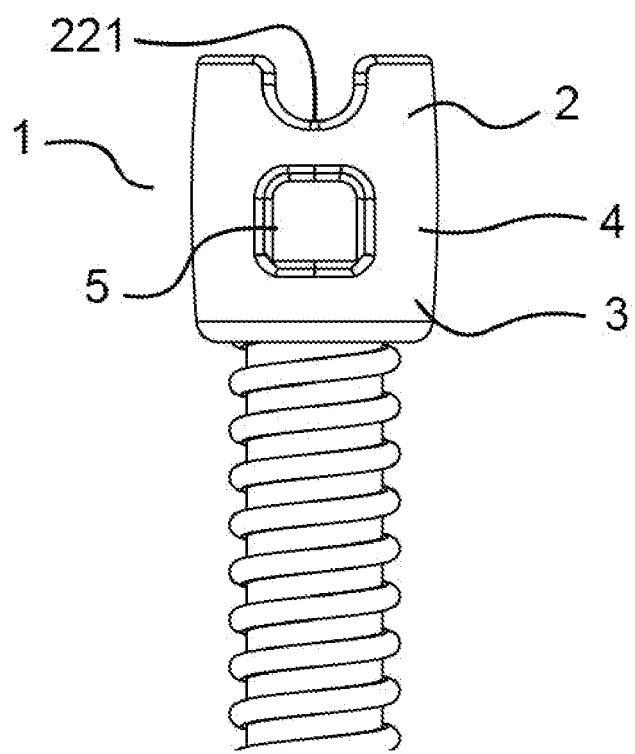
FIG. 3 is a side view of a hose connector with an adjustment structure in accordance with an example embodiment.
Figure 4:
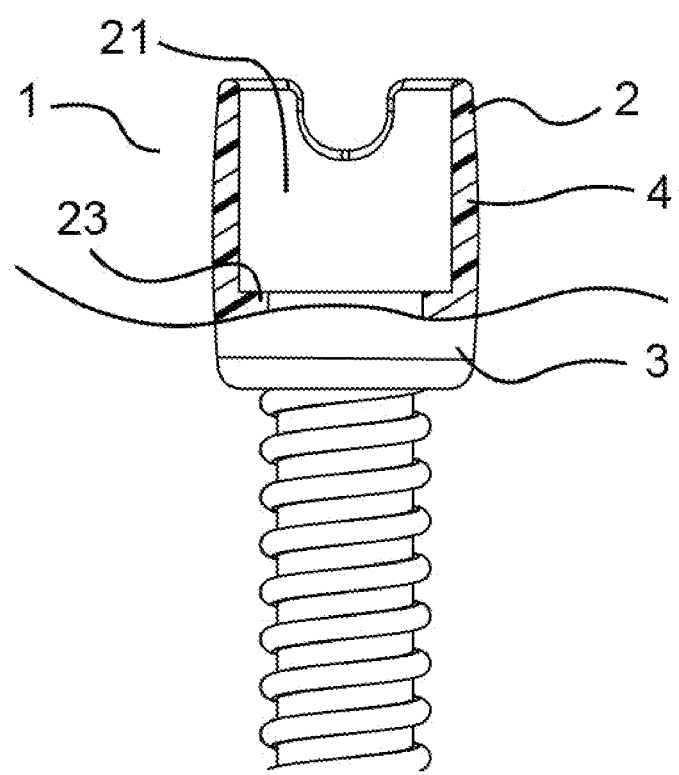
FIG. 4 is a cross-sectional view of a hose connector with an adjustment structure in accordance with an example embodiment.
Figure 5:
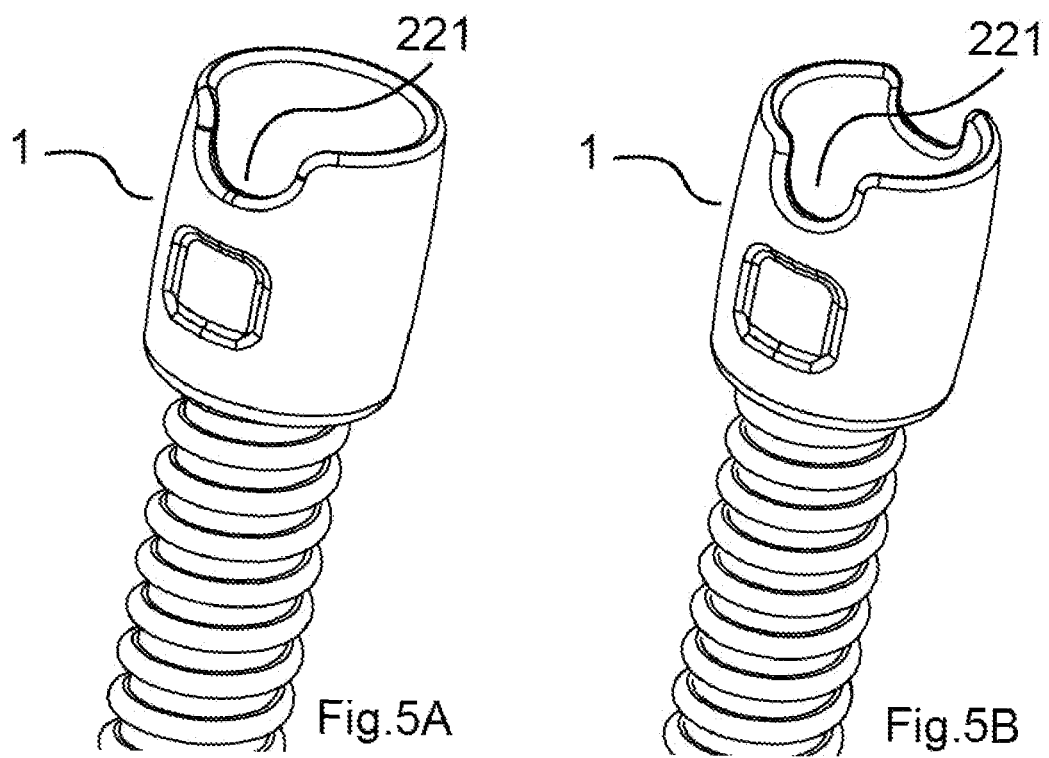
FIG. 5A and FIG. 5B are schematic diagrams of a hose connector with one adjustment structure and another hose connector with more adjustment structures, in accordance with an example embodiment.
Figure 6:
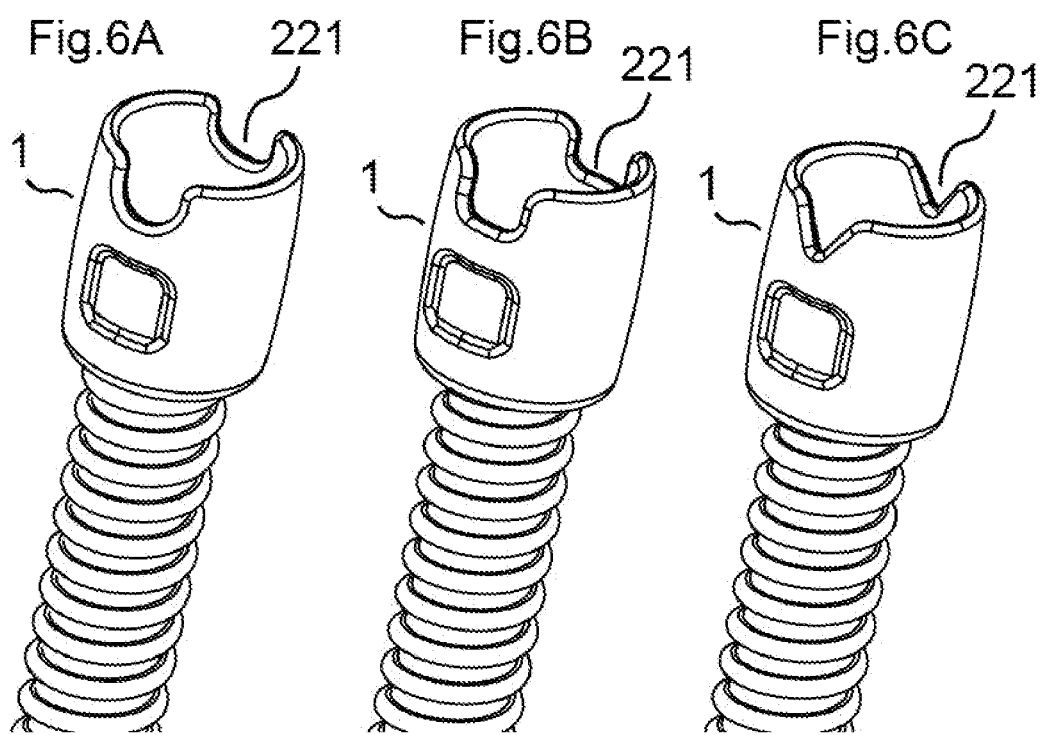
FIG. 6A, FIG. 6B, and FIG. 6C are three schematic diagrams illustrating different forms of the adjustment structure in a hose connector in accordance with an example embodiment.
Figure 7:
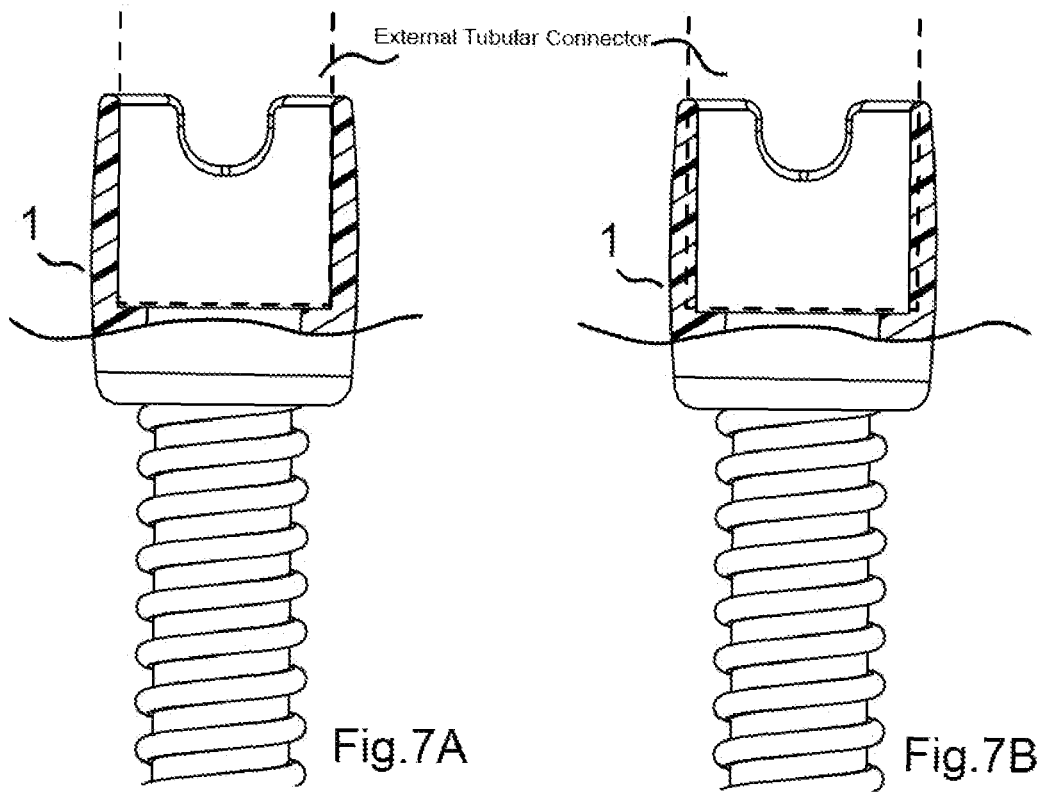
FIG. 7A and FIG. 7B are two schematic diagrams illustrating different internal diameters of a hose connector with an adjustment structure in accordance with an example embodiment.
Figure 8:
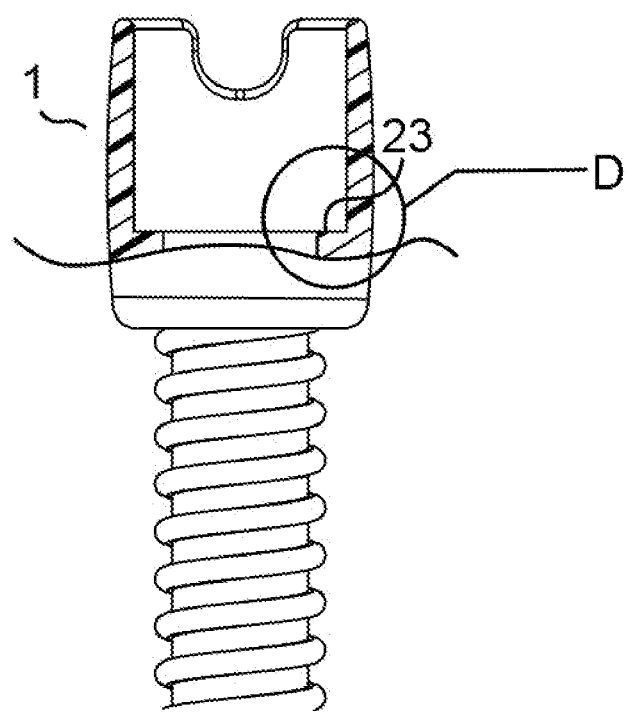
FIG. 8 is a schematic diagram showing a form of the abutment surface of a hose connector with an adjustment structure in accordance with an example embodiment.
Figure 9:
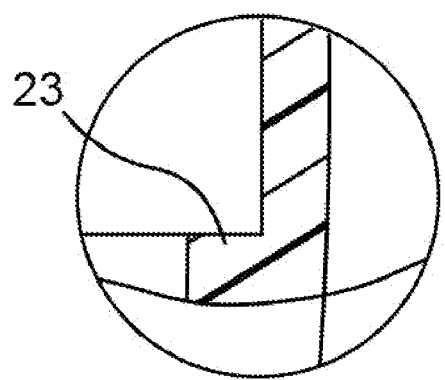
FIG. 9A and FIG. 9B are schematic diagrams illustrating different forms of the abutment surface D shown in FIG. 8.
Figure 9:
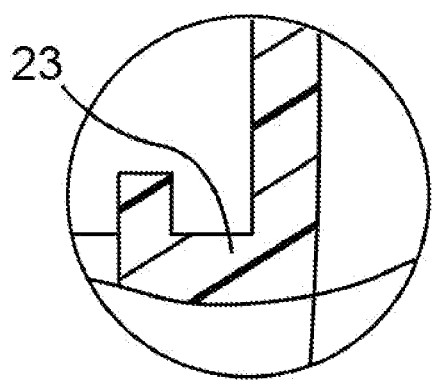
Figure 10:
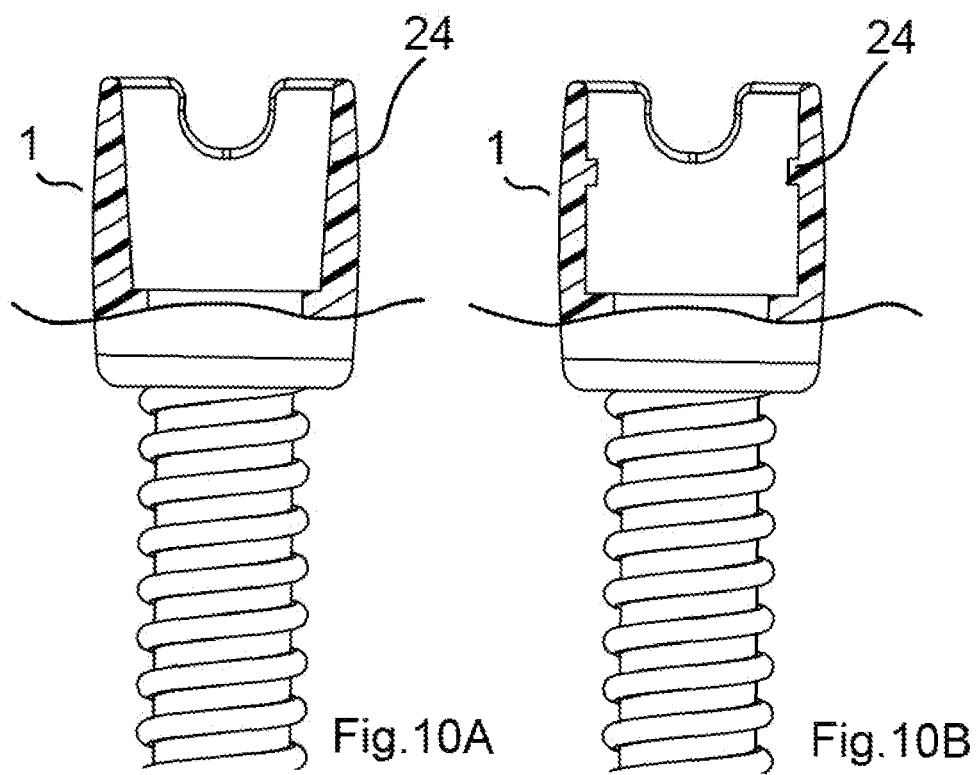
FIG. 10A and FIG. 10B are schematic diagrams showing different forms of the retaining structure of a hose connector with an adjustment structure in accordance with an example embodiment.
Figures 11A, 11B, 11C:
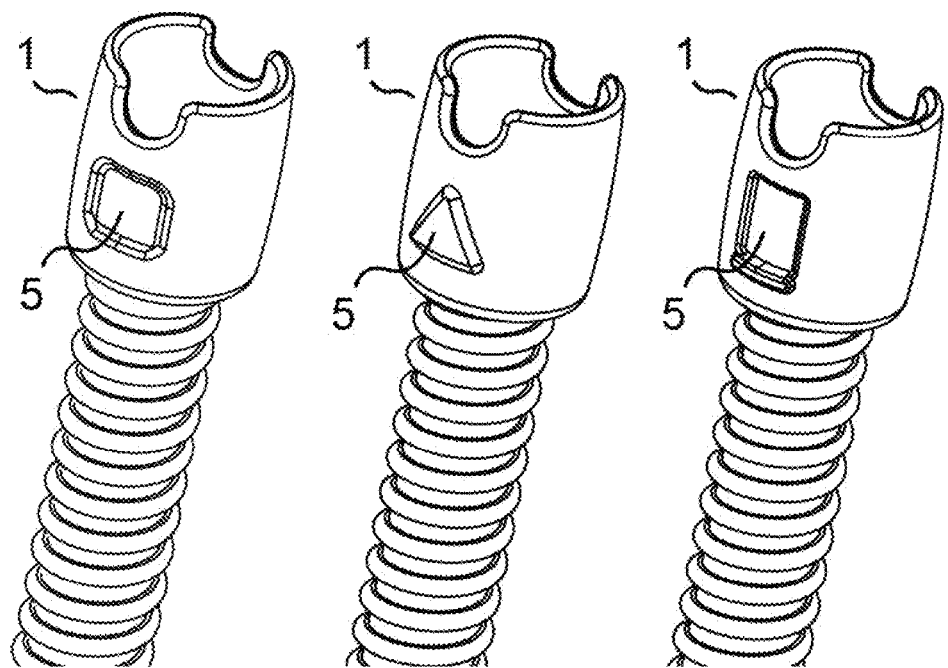
FIGS. 11A, 11B, 11C are schematic diagrams illustrating different forms of the gripping portion of a hose connector with an adjustment structure in accordance with an example embodiment.
Figures 12A, 12B:
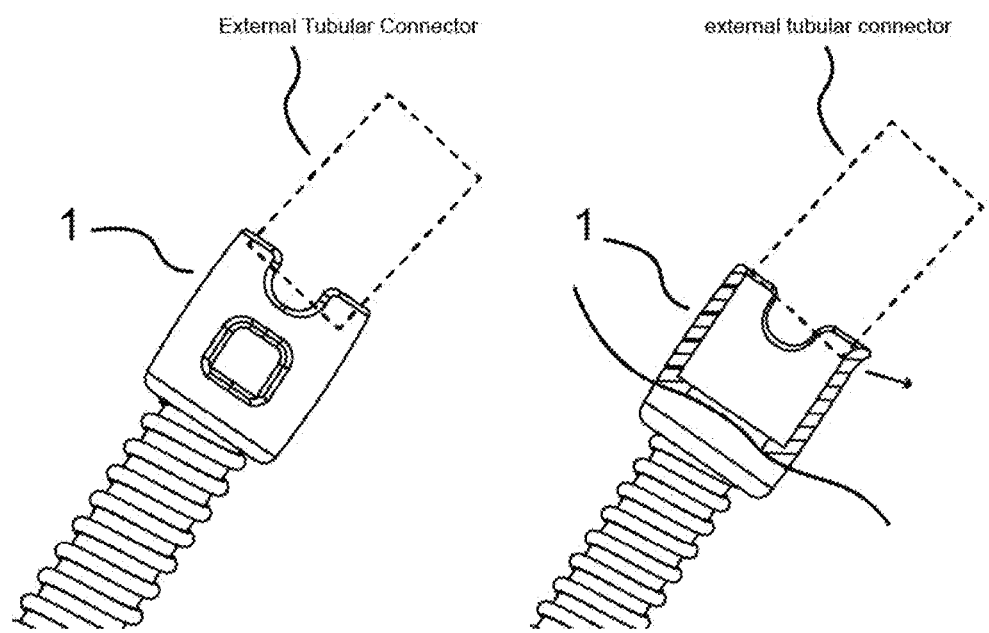
FIGS. 12A, 12B are installation diagrams of a hose connector with an adjustment structure in accordance with an example embodiment.

As shown in FIG. 1, the opening of the first connector end of the hose connector is innovatively configured to have an adjustment structure (i.e., the opening of the first connector end is discontinuous), and the inner diameter of the opening of the first connector end is configured to be smaller than or equal to the outer diameter of external components (such as external tubular connectors). While maintaining the sealing performance of the hose connector, as shown in FIGS. 12A. 12B, it is easier to assemble and disassemble with external components, thereby extending the overall service life of the hose connector. However, the design of the adjustment structure is subject to certain limitations. Since stress is concentrated on the adjustment structure, materials that are too brittle or a design of the adjustment structure that is too sharp may lead to the initiation of cracks at the root of the adjustment structure, becoming a source of fracture. To obtain a user-friendly and durable hose connector, the disclosure comprehensively considers the boundary conditions of the adjustment structure (i.e., the interaction mode of the structure with other parts, such as the assembly and disassembly of the opening of the first connector end with external components), mechanical properties of materials (such as yield strength, elastic modulus, fatigue limit, etc.), environmental factors (such as temperature, humidity, etc.), deformation and displacement (such as bending, stretching, twisting, etc.), assembly and manufacturing tolerances, and the maximum load that the first connector end can withstand. It is determined that the hose connector in this disclosure is made of elastic material with a hardness of Shore A 30-70, and the root of the adjustment structure is smooth and without sharp cross points. In use, the adjustment structure at the first connector end is prone to stress concentration, more likely to undergo elastic deformation to produce a larger opening for efficient assembly with external components, and through the elastic properties of the material to undergo corresponding deformation to restore the size and shape of the opening, achieving the purpose of sealingly connecting external components.

The following specific embodiments illustrate several structures of the hose connector 1 with the adjustment structure in this disclosure.

Embodiment 1

As shown in FIGS. 1-3 and 11A-11C, the hose connector 1 includes a first connector end 2 configured to connect to an external tubular connector, a second connector end 3 configured to connect to a hose, and a sidewall 4 configured to encircle and form a first connector end 2 and a second connector end 3. The sidewall 4 has an interior and an exterior, with the exterior configured to provide a sufficient gripping area for the user, namely the gripping portion 5. The gripping portion 5 can be in the form of a recess or protrusion, by providing a pattern of undercuts or protrusions to increase friction. These patterns can be circular, oval, square, triangular, or any other shape that can increase friction; the sidewall 4 of the hose connector 1 is made of a first material 6 with elasticity, which can be rubber, silicone, thermoplastic elastomer, etc., with a hardness of Shore A at or between 30 to 70; the overall height of the hose connector 1 is approximately at or between 15 to 45 mm, the overall internal diameter does not exceed 22 mm, and the overall thickness is not less than 1 mm.

As shown in FIGS. 1-10, the first connector end 2 is configured to connect and accommodate an external tubular connector, and the internal diameter of the first connector end 2 is smaller than or equal to the outer diameter of the external tubular connector. The first connector end 2 includes part of the sidewall 4 of the hose connector 1 (thus the first connector end 2 includes the first material 6), a chamber 21 for accommodating the external tubular connector, an opening 22 allowing the external tubular connector to enter the chamber 21, an abutment surface 23 to restrict the displacement of the external tubular connector, and a retaining structure 24 to enhance fixing capability: part of sidewall 4 of the hose connector 1 extends from the opening 22 of the first connector end 2 to the abutment surface 23, and the part of sidewall 4 has a non-uniform wall thickness. To avoid easy breakage of the first connector end 2 due to frequent assembly and disassembly, the wall thickness at the abutment surface 23 is thicker than the wall thickness at the opening 22, with the wall thickness at the sidewall 4 at the abutment surface 23 being at least 2 mm. The sidewall 4 internally forms a chamber 21 to accommodate an external tubular connector. To ensure a stable connection between the external tubular connector and the first connector end 2, the chamber 21 needs to provide sufficient contact surface for the external tubular connector, with the depth of the chamber 21 being at least 12 mm. The opening 22 of the first connector end 2 is configured to interact with the external tubular connector (i.e., allowing the external tubular connector to enter the chamber 21). To ensure the airtightness of the hose connector 1, the inner diameter of the opening 22 does not exceed 22 mm. To facilitate deformation of the opening 22, at least one adjustment structure 221 is provided on the opening 22, and the form of the adjustment structure 221 is a notch. To prevent the adjustment structure 221 from cracking or breaking during use, the wall thickness at the opening 22 is considered along with the stress design and the yield strength of the chosen material, ensuring it is no less than 2 mm. The depth is adjusted considering the hardness, thickness, other characteristics of the used material, and the width of the adjustment structure 221, but not exceeding ½ of the depth of the chamber 21, preferably not more than ⅔ of the depth of the chamber, and more ideally no more than ¼ of the depth of the chamber, with a width of the adjustment structure 221 less than ⅔ of the inner diameter of the opening 22. In some implementations, the width of the adjustment structure 221 is less than ½ of the inner diameter of the opening 22; or in other implementations, the width of the adjustment structure 221 is less than ⅓ of the inner diameter of the opening 22. At least part of the root of the adjustment structure 221 has an arc shape, and its general form can be arc-shaped, square with rounded corners, or V-shaped with rounded corners (in other implementations, the thickness of the adjustment structure 221 is not less than 2 mm, its depth does not exceed ⅔ of the depth of chamber 21, and its width is less than ½ of the inner diameter of the opening 22, with the root of the adjustment structure 221 possibly not having an arc shape). The abutment surface 23 is configured to extend from part of the sidewall 4 of the hose connector 1 towards the central axis of the hose connector 1, dividing the hose connector 1 into the first connector end 2 and the second connector end 3. To effectively limit the distance the external tubular connector enters the first connector end 2 and to ensure overall ventilation, the width of the protruding part of the abutment surface 23 is at or between 1 to 10 mm, with a height of at least 1 mm (in other implementations, the hose connector may not have an abutment surface 23). The retaining structure 24 extends from part of the sidewall 4 of the hose connector 1 towards the central axis of the hose connector 1. The retaining structure 24 is configured to contact the external tubular connector and further enhance the securing ability of the first connector end 2 (i.e., the capacity to form a secured connection with the external tubular connector). The inner diameter of the retaining structure 24 is less than or equal to the outer diameter of the external tubular connector and smaller than the inner diameter of the first connector end 2. The retaining structure 24 can either take the form of protruding toward a central axis of the hose connector 1 or be in an inverted cone shape (with the inner diameter gradually decreasing from the opening 22 to the abutment surface 23). To prevent the inner diameter from being too small, which would hinder the complete entry of the external tubular connector into the chamber 21, the protrusion should not exceed 3 mm. The maximum inner diameter of the cone shape should be less than or equal to the outer diameter of the external tubular connector, and the inner diameter of the retaining structure 24 should not be less than 16 mm. When the retaining structure 24 is in an inverted cone shape, its height can equal the depth of the chamber 21. When in a protruding form, the protruding height of the protruding retaining structure should be less than the depth of the chamber 21 and can be a step with a height that is at or between 1 to 5 mm. In other implementations, the retaining structure 24 can be made from a second material that is harder than the first material 6, such as silicone, rubber, or thermoplastic elastomer with a Shore A hardness of at or between 60 to 80. In further implementations, the first connector end 2 may not have a retaining structure 24.

The second connector end 3 is configured to connect to a hose and includes part of the sidewall 4 of the hose connector 1 and a space to accommodate the hose. In this embodiment, the structure of the second connector end 3 is different from that of the first connector end 2, distinguished by the fact that the inner diameter of the second connector end 3 is less than or equal to that of the first connector end 2. In some implementations, the inner diameter of the first connector end 2 is greater than that of the second connector end 3.

In this embodiment, patients can, at the adjustment structure 221, combine the external tubular connector with the hose connector 1 at a certain angle, as shown in FIGS. 12A, 12B, which facilitates deformation at the adjustment structure 221.

In other implementations, the structure of the second connector end 3 differs from that of the first connector end 2. The second connector end 3 can have other retaining structures 24, such as clips or snap-fits, for a secure connection with the hose.

In further implementations, the hose connector can be made of rigid materials, such as polyethylene, polypropylene, polycarbonate, etc. The adjustment structure 221 enhances the deformability of the first connector end 2.

Embodiment 2

The hose connector 1 includes a first connector end 2 configured to connect to an external tubular connector, a second connector end 3 configured to connect to a hose, and a sidewall 4 configured to encircle and form a first connector end 2 and a second connector end 3. The sidewall 4 has an interior and an exterior, with the exterior configured to provide a sufficient gripping area for patients, i.e., the gripping portion 5. The first connector end 2 is configured to connect to and accommodate a hose connector, including part of the sidewall 4 of the hose connector 1, a chamber 21 to accommodate the external tubular connector, an opening 22 to allow the external tubular connector to enter the chamber 21, an abutment surface 23 to limit the displacement of the external tubular connector, and a retaining structure 24. The difference between the hose connector 1 provided in this embodiment and the hose connector 1 in Embodiment 1 is that the opening 22 of the first connector end 2 does not have an adjustment structure 221 that is in the form of a notch. As shown in FIG. 13, the sidewall 4 of the hose connector 1 in this embodiment is made from a combination of a first material 6 with elasticity and a third material 7 that is softer than the first material 6 (or made from a third material 7 different from the first material 6). The third material 7 can be rubber, silicone, thermoplastic elastomer, etc., with a hardness of Shore A at or between 20 to 40. The third material 7 is provided at the opening 22 of the first connector end 2, making the opening 22 more prone to deformation to accommodate the external tubular connector.

The hose connector with an adjustment structure provided herein has at least the following beneficial effects:

1) The design of the adjustment structure addresses a common issue in many hose connectors, where the inner diameter of the connector is typically larger than the external diameter of the connected external component (including the external tubular connector). This design ensures a smooth connection between the external component and the hose connector. To enhance the durability of the hose connector, some hose connectors opt for rigid materials like polyethylene, polypropylene, polycarbonate, or other plastic materials. However, to improve user experience and product comfort, others choose elastic materials such as silicone, rubber, or other thermoplastic elastomers, which offer softness and strong deformation capabilities. Therefore, using rigid materials does not provide a better experience than using elastic ones, but elastic materials are prone to fatigue deformation or material aging due to repeated stress loading and unloading as the connector needs frequent installation and disassembly with external components, gradually losing their original shape and elasticity, leading to seal failure and slippage. This disclosure innovatively combines the principle of notch effect by incorporating an adjustment structure with a certain depth and width at the opening of the first connector end. This design facilitates deformation when connecting to the external tubular connector. The notch effect causes stress concentration at the discontinuous opening when the external tubular connector contacts the discontinuous opening with an adjustment structure. This stress concentration at the opening reaches the yield strength of the material, resulting in elastic deformation in the region near the root of the adjustment structure. This leads to a larger opening to accommodate the external component quickly and easily. Through reasonable material selection and design, the adjustment structure can return to its original size and shape after expansion, ensuring a sealed connection with the external component. This provides a comfortable user experience, effective sealing, and an extended lifespan for the hose connector during patient use of the hose connector. The connector of the hose connector is made from an elastic material that feels comfortable, and the inner diameter of the connector is configured to be less than or equal to the outer diameter of the external component. At least one adjustment structure is provided on the opening:

a. In comparison to hose connectors on the market that reduce the inner diameter of the connector, the connector described herein is provided with at least one adjustment structure, and the inner diameter is less than or equal to the outer diameter of the external component. While ensuring the ability to provide the same level of extension of the hose connector's lifespan, this design offers a flexible structure, enhancing the operability and adaptability of the connector. It allows connectors that are originally equal or slightly smaller in inner diameter to deform into a larger opening through the adjustment structure, facilitating smooth entry of the external component and preventing issues arising from the inner diameter of the connectors being too small to connect to other external components.

b. In contrast to hose connectors on the market that enlarge the inner diameter of the connector, the connector discussed herein has a larger proportion of an effective sealing portion within the connector. Many hose connectors on the market, due to the enlargement of the inner diameter of the connector, allow a smooth connection to external components but may result in a certain distance between the effective sealing portion and the inner diameter of the end surface. This indirectly reduces the proportion of the effective sealing portion in the chamber accommodating the external connector. However, the connector with at least one adjustment structure ensures that the sealing portion occupies one hundred percent of the chamber containing the external connecting component, increasing the contact area with the external component and achieving a better sealing effect.

2) The installation and disassembly experimental validation of the connector of the hose connector with the structural design of the adjustment structure, combined with material selection, can prolong the service life of the connector. Due to the use of elasticity materials that can deform, the elastic material of the connector undergoes fatigue deformation due to prolonged and frequent installation and disassembly, leading to the loosening of the connector and the inability to achieve sealing. Therefore, in the design provided herein, the inner diameter of the connector is configured to be smaller than or equal to the outer diameter of the external component. The extended lifespan of hose connectors means that users can reduce the frequency of replacing the hose connector, making it more economical for them. Additionally, this reduction in replacement frequency leads to less waste disposal, making it more environmentally friendly.

The various technical features of the embodiments described above can be combined in any way. To keep the description concise, not all possible combinations of the technical features in the above embodiments have been described. However, as long as these combinations of technical features are not contradictory, they should be considered within the scope documented in this specification. It must be noted that as used herein and in the appended claims, the singular forms "a", "an", and "the" include their plural equivalents, unless the context clearly dictates otherwise.

The embodiments described above only represent several implementation methods of the disclosure. While the descriptions are specific and detailed, they should not be understood as limiting the scope of the patent. It should be noted that ordinary skilled artisans in this field can make various modifications and improvements without departing from the conceptual framework of the disclosure. All such modifications and improvements are within the scope of protection of the present disclosure. Therefore, the scope of protection of the patent for this disclosure is determined by the appended claims.

The invention claimed is:

1. A hose connector with at least one adjustment structure, comprising:

a sidewall configured to encircle and form a first connector end and a second connector end and provided with an interior and an exterior, with the exterior having a gripping portion;

wherein the first connector end, configured to connect to an external tubular connector, includes a chamber to house the external tubular connector, an opening to allow the external tubular connector to enter the chamber, and an abutment surface to limit a displacement of the external tubular connector;

wherein the second connector end, configured to connect to a hose, includes a space to accommodate the hose;

wherein the at least one adjustment structure is provided in the sidewall along the opening;

wherein the first connector end is made of a resilient first material, a hardness of the first material is between Shore A 30 to Shore A 70; and wherein the first connector end has a non-uniform wall thickness from the abutment surface to the opening, and the wall thickness is configured to be greater at the abutment surface than at the opening, wherein the at least one adjustment structure has a third material different from the first material such that the first connector end is configured to elastically deform when connecting to the external tubular connector by causing stress concentration at the at least one adjustment structure, wherein the third material has a hardness that is less than the hardness of the first material and is between Shore A 20 and Shore A 40.

2. The hose connector with the at least one adjustment structure according to claim 1, wherein the inner diameter of the opening of the first connector end does not exceed 22 mm.

3. The hose connector with the at least one adjustment structure according to claim 1, wherein an overall height range of the hose connector is between at or about 15 mm to at or about 45 mm.

4. The hose connector with the at least one adjustment structure according to claim 1, wherein the wall thickness at the opening of the first connector end is not less than 2 mm.

5. The hose connector with the at least one adjustment structure according to claim 1, wherein an inner diameter of the second connector end is less than or equal to the inner diameter of the first connector end.

6. A hose connector with at least one adjustment structure, comprising:

a sidewall configured to encircle and form a first connector end and a second connector end and provided with an interior and an exterior, with the exterior having a gripping portion;

wherein the first connector end, configured to connect to an external tubular connector, includes a chamber to house the external tubular connector, an opening to allow the external tubular connector to enter the chamber, and a retaining structure to enhance fixation ability;

wherein the second connector end, configured to connect to a hose, includes a space to accommodate the hose;

wherein the at least one adjustment structure is provided in the sidewall along the opening;

wherein the first connector end is made of a resilient first material, a hardness of the first material is between Shore A 30 to Shore A 70; and wherein the retaining structure has one or more of the following characteristics:

a. having an inner diameter less than or equal to an outer diameter of the external tubular connector;
b. protruding toward a central axis of the hose connector;
c. being in an inverted cone shape;
d. a material of the retaining structure being a second material, wherein the at least one adjustment structure has a third material different from the first material such that the first connector end is configured to elastically deform when connecting to the external tubular connector by causing stress concentration at the at least one adjustment structure, wherein the third material has a hardness that is less than the hardness of the first material and is between Shore A 20 and Shore A 40.

7. The hose connector with the at least one adjustment structure according to claim 6, wherein an inner diameter of the second connector end is less than or equal to the inner diameter of the first connector end.

8. The hose connector with the at least one adjustment structure according to claim 6, wherein a height of the retaining structure in the inverted cone shape is equal to a depth of the chamber.

9. The hose connector with the at least one adjustment structure according to claim 6, wherein a maximum inner diameter of the retaining structure in the inverted cone shape is less than or equal to the outer diameter of the external tubular connector.

10. The hose connector with the at least one adjustment structure according to claim 6, wherein a depth of the chamber is at least 12 mm.

11. The hose connector with the at least one adjustment structure according to claim 6, wherein a protruding height of the retaining structure having the characteristic of protruding toward a central axis of the hose connector is less than a depth of the chamber.

12. A hose connector with at least one adjustment structure, comprising:

a sidewall configured to encircle and form a first connector end and a second connector end and provided with an interior and an exterior, with the exterior having a gripping portion;

wherein the first connector end, configured to connect to an external tubular connector, includes a chamber to house the external tubular connector, an opening to allow the external tubular connector to enter the chamber, and an abutment surface to limit a displacement of the external tubular connector;

wherein the second connector end, configured to connect to a hose, includes a space to accommodate the hose;

wherein the at least one adjustment structure is provided in the sidewall along the opening;

wherein the first connector end is made of a resilient first material, a hardness of the first material is between Shore A 30 to Shore A 70;

wherein an inner diameter of the second connector end is less than or equal to an inner diameter of the first connector end; and wherein a depth of the chamber is at least 12 mm, wherein the at least one adjustment structure has a third material different from the first material such that the first connector end is configured to elastically deform when connecting to the external tubular connector by causing stress concentration at the at least one adjustment structure, wherein the third material has a hardness that is less than the hardness of the first material and is between Shore A 20 and Shore A 40.

13. The hose connector with the at least one adjustment structure according to claim 12, wherein the inner diameter of the first connector end is less than or equal to an outer diameter of the external tubular connector.

14. The hose connector with the at least one adjustment structure according to claim 12, wherein the first connector end has a retaining structure and an inner diameter of the retaining structure is less than the inner diameter of the first connector end.

15. The hose connector with the at least one adjustment structure according to claim 12, wherein the gripping portion is in a form of a recess or protrusion.

16. The hose connector with the at least one adjustment structure according to claim 12, wherein a depth of the at least one adjustment structure does not exceed ½ of the depth of the chamber.

17. A hose connector with at least one adjustment structure, comprising:
- a sidewall configured to encircle and form a first connector end and a second connector end and provided with an interior and an exterior, with the exterior having a gripping portion;
- wherein the first connector end, configured to connect to an external tubular connector, includes a chamber to house the external tubular connector, an opening to allow the external tubular connector to enter the chamber, and an abutment surface to limit a displacement of the external tubular connector;
- wherein the second connector end, configured to connect to a hose, includes a space to accommodate the hose;
- wherein the first connector end is made of a resilient first material, a hardness of the first material is between Shore A 30 to Shore A 70;
- wherein the at least one adjustment structure is provided in the sidewall along the opening; and
- wherein the at least one adjustment structure has the following characteristics:
  a. having a depth not exceeding ½ of a depth of the chamber;
  b. having a width less than ⅔ of an inner diameter of the opening of the first connector end,
- wherein the at least one adjustment structure has a third material different from the first material such that the first connector end is configured to elastically deform when connecting to the external tubular connector by causing stress concentration at the at least one adjustment structure,
- wherein the third material has a hardness that is less than the hardness of the first material and is between Shore A 20 and Shore A 40.

18. The hose connector with the at least one adjustment structure according to claim 17, wherein the inner diameter of the first connector end is less than or equal to an outer diameter of the external tubular connector.

19. The hose connector with the at least one adjustment structure according to claim 17, wherein a root of the at least one adjustment structure has an arc shape.

* * * * *